United States Patent
Weisse et al.

[11] Patent Number: 5,395,978
[45] Date of Patent: Mar. 7, 1995

[54] PROCESS FOR SELECTIVE PREPARATION OF HYDROXYBENZALDEHYDES

[75] Inventors: Laurent Weisse, Oberursel; Robert Neunteufel, Bad Nenndorf; Heinz Strutz, Usingen, all of Germany

[73] Assignee: Hoechst Aktiengesellschaft, Frankfurt am Main, Germany

[21] Appl. No.: 154,255

[22] Filed: Nov. 18, 1993

[30] Foreign Application Priority Data

Nov. 20, 1992 [DE] Germany ............. 42 39 101.6

[51] Int. Cl.$^6$ ............................................. C07C 45/49
[52] U.S. Cl. .................................................... 568/428
[58] Field of Search ..................... 568/311, 322, 428

[56] References Cited

U.S. PATENT DOCUMENTS

| | | | |
|---|---|---|---|
| 2,485,237 | 10/1949 | Gresham et al. | 568/428 |
| 3,098,875 | 7/1963 | Schmerling | 260/600 |
| 3,948,998 | 4/1976 | Fujiyama et al. | 568/428 |
| 4,368,336 | 11/1983 | Fujiyama et al. | 568/428 |
| 4,460,794 | 7/1984 | Fujiyama et al. | 568/428 |
| 5,208,383 | 5/1993 | Takefumi et al. | 568/322 |
| 5,235,109 | 8/1993 | Langi et al. | 568/322 |

FOREIGN PATENT DOCUMENTS

| | | | |
|---|---|---|---|
| 2422197 | 11/1974 | Germany | 568/428 |
| 63-2943 | 1/1988 | Japan | 568/311 |

OTHER PUBLICATIONS

Chemical Abstracts, vol. 070, No. 7, "Reaction of phenol with carbon monoxide under high pressure in the medium of hydrogen fluoride and boron fluoride", Feb. 17, 1969.

*Primary Examiner*—James H. Reamer
*Attorney, Agent, or Firm*—Connolly & Hutz

[57] ABSTRACT

Process for preparing hydroxybenzaldehydes of the formula (1)

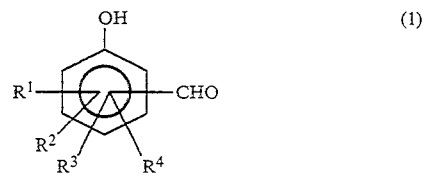

in which $R^1$-$R^4$ are hydrogen, fluorine, chlorine, bromine, alkyl, alkoxy, phenyl, naphthyl, phenylalkyl, naphthylalkyl, phenoxy or saturated or unsaturated cyclopentane or cyclohexane radicals, and $R^1$-$R^4$ may with the hydroxybenzene ring carbon atoms on which they are located form 1 or 2 saturated or unsaturated isocyclic or heterocyclic rings, by admixing 1 mol of a phenol of the formula (2)

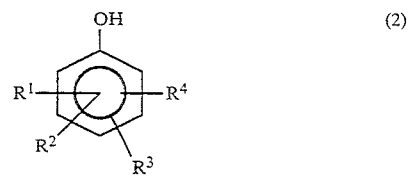

in which $R^1$-$R^4$ have the stated meanings, in a pressure vessel with from 5 to 100 mol of hydrogen fluoride and from $0.5+x$ to $1.5+x$ mol of boron trifluoride, where x is the number of oxygen atoms contained in the starting compound (formula (2)), setting the mixture to from $-10°$ to $100°$ C. and then passing carbon monoxide into this mixture until a pressure of from 10 to 150 bar is reached and allowing the mixture to react at the desired pressure reached.

17 Claims, No Drawings

PROCESS FOR SELECTIVE PREPARATION OF HYDROXYBENZALDEHYDES

The present invention relates to an improved, technically simple process for preparing hydroxybenzaldehydes by selective formylation of phenol and phenol derivatives to give the corresponding hydroxybenzaldehydes.

Hydroxybenzaldehydes are important intermediates for cinnamic acid derivatives, which are used as UV absorbers in the cosmetics industry, and also for optical brighteners, dyes and pharmaceutical and crop protection products (DE-OS 27 32 227). 3,5-Dialkyl-4-hydroxybenzaldehydes are used as antioxidants (U.S. Pat. No. 3,974,223). In addition, they are important starting materials in the synthesis of benzoxazines, a class of compounds which is of technical interest particularly in the area of crop protection (EP 289 171). They are furthermore important intermediates for industrial syntheses of fragrances and photographic chemicals (EP 451 650).

For the preparation of hydroxybenzaldehydes a number of processes are known, as can be seen in practically every textbook on organic chemistry (Houben-Weyl E3, 4th edition). However, all these processes have one or more of the following disadvantages: formation of difficult-to-separate isomers, multistage synthesis, formation of a large amount of salts, low yields, starting materials difficult-to-obtain (DE 29 04 315, DE-OS 27 36 523).

A known direct method for preparing hydroxybenzaldehydes is the carbonylation of the corresponding phenols. However, it has been shown that phenols cannot be carbonylated by means of the Gattermann-Koch reaction (Advanced Organic Chemistry, 1983, McGraw-Hill, 494). In addition, the amount of aluminum chloride used leads to considerable waste water problems.

The formylation of phenols with orthoformic ester dichloride or orthoformic ester and aluminum trichloride or titanium tetrachloride in excess is industrially untenable because of the poor yields, the low selectivity and the associated separation problems, and the waste water problems associated with the use of large amounts of metal halides (Chem. Ber. 96 (1963) 308).

The use of a large excess of urotropin in the Duff reaction also leads to waste water pollution (BE 841 523, DE 33 04 202). In addition the yields are mostly small (Advanced Organic Chemistry, 1983, McGraw-hill, Tokyo, 496).

DE-OS 27 32 227 describes the Gattermann reaction with hydrogen cyanide in hydrogen fluoride, which however leads to considerable safety problems.

It is furthermore known that phenol derivatives, such as guaiacol, can be carbonylated with methyl formate in a hydrogen fluoride/boron trifluoride mixture (EP 300 861). However, this reaction mostly leads to product mixtures and requires a very large excess of boron trifluoride.

It is also known that phenol can be converted with carbon monoxide in hydrogen fluoride/boron trifluoride into p-hydroxybenzaldehyde (Sekiyu Gakkai Shi 11 (1968) 690). For complete conversion by this method a carbon monoxide pressure of 300 bar is required, which results in 61 and 13 mol percent respectively of para- and ortho-hydroxybenzaldehyde, i.e. a mixture of isomers, being formed.

It is therefore an object of the present invention to provide a selective process for preparing hydroxybenzaldehydes, whereby the disadvantages inherent in the known processes are avoided.

It has now been surprisingly found that hydroxybenzaldehydes of the general formula (1)

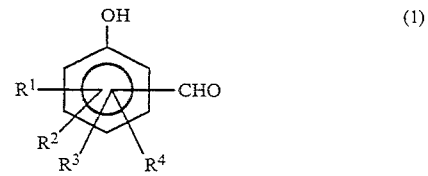

in which $R^1$, $R^2$, $R^3$ and $R^4$ are identical or different and are hydrogen, fluorine, chlorine or bromine atoms, also alkyl($C_1$–$C_6$) groups which may be substituted by fluorine atoms, alkoxy($C_1$–$C_4$) groups, aryl($C_6$–$C_{14}$) groups such as for example phenyl or naphthyl groups which may be substituted at the aromatic nucleus by fluorine, chlorine or bromine atoms or by alkyl($C_1$–$C_4$) or alkoxy($C_1$–$C_4$) groups, also aryl($C_6$–$C_{14}$)-alkyl($C_1$–$C_6$) groups such as for example phenylalkyl($C_1$–$C_6$) or naphthylalkyl($C_1$–$C_6$) groups, which may be substituted at the aryl radical by fluorine, chlorine or bromine atoms or by alkyl($C_1$–$C_4$) or alkoxy($C_1$–$C_4$) groups, also the radical of a five- or six-membered saturated or unsaturated carbocycle, for example a cyclopentyl, cyclopentadienyl, cyclohexyl, cyclohexenyl or cyclohexadienyl group which may be substituted by alkyl($C_1$–$C_4$) groups, also aryl($C_6$–$C_{10}$)oxy groups, for example the phenoxy group which may be substituted at the aromatic nucleus by fluorine, chlorine or bromine atoms or by alkyl($C_1$–$C_4$) or alkoxy($C_1$–$C_4$) groups, and where the substituents $R^1$, $R^2$, $R^3$ and $R^4$ may with the hydroxybenzene ring carbon atoms on which they are located form one or two saturated or unsaturated isocyclic or heterocyclic rings which may be substituted for example by alkyl($C_1$–$C_4$) groups, and in which the hydroxyl and aldehyde groups are in the ortho or para position with respect to one another can be prepared in an advantageous manner by admixing 1 mol of a phenol of the general formula (2)

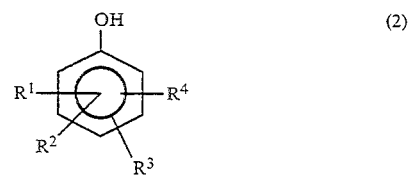

in which $R^1$, $R^2$, $R^3$ and $R^4$ have the above meanings, if desired in an organic solvent which is inert towards the reactants, in a pressure vessel with from about 5 to about 100 mol, preferably from about 20 to about 50 mol of hydrogen fluoride and from about 0.5+x to about 1.5+x mol, preferably from about 0.9+x to about 1.2+x mol, where x is the number of oxygen atoms contained in the starting compound of the stated formula (2), particularly preferably with 1 mol of boron trifluoride, setting the temperature of this mixture to from about −10° to about 100° C, preferably from about 0° to about 80° C., and subsequently passing carbon monoxide into this initially charged mixture until a pressure of from about 10 to about 150 bar, preferably from about 20 to 100 bar, is reached and allowing the mixture to react at the desired pressure reached.

Further details of the process of the invention are:

Organic solvents which are inert towards the reactants are, for example, methylene chloride, chloroform, carbon tetrachloride, dichloroethane, hexane and heptane. However, the reaction is preferably carried out with pure anhydrous hydrogen fluoride, i.e. in the absence of an inert solvent.

The reaction times generally vary between about 30 minutes and about 50 hours, preferably between about 1 hour and about 24 hours.

Preferably the compound of the stated general formula (2) is introduced first and the hydrogen fluoride is then added, although the opposite order of addition is also possible. Subsequently the boron trifluoride is expediently added all at once. However, the addition can also be carried out in steps. After reaching the desired reaction temperature the desired carbon monoxide pressure is set and readjusted during the reaction if required. However, the carbon monoxide pressure can also be set so that no readjustment during the reaction is needed.

The particular optimal temperatures within the abovementioned general and preferred temperature range are to be selected and used in accordance with the particular starting compound of the stated formula (2) which is used, i.e. in accordance with the substituents located on the benzene nucleus of the starting compound.

The process of the invention is notable for the fact that differently substituted hydroxybenzaldehydes can be obtained by a simple and short synthesis (single-stage process) very selectively and in up to quantitative yields. In comparison with the processes of the prior art it has the advantage that even at relatively low pressure high yields and selectivities can be achieved. A further advantage is that it is basically possible to recover the catalytic hydrogen fluoride and boron trifluoride.

The examples below illustrate the process of the invention without limiting it to them.

EXAMPLE 1

Preparation of 4-hydroxybenzaldehyde 9.41 g (100 mmol) of phenol are admixed in a 250 ml stainless-steel autoclave with 100 g (5 mol) of anhydrous hydrogen fluoride and 14 g (206 mmol) of boron trifluoride. Subsequently the reaction mixture is heated to 40° C. and carbon monoxide is passed in until the pressure has reached 50 bar. This pressure has to be readjusted a number of times during the reaction time. After one hour the reaction solution is poured onto 1 kg of ice and is neutralized with concentrated KOH solution. After extracting the aqueous phase a number of times with ethyl acetate the combined organic phases are dried with $MgSO_4$. The solvent is distilled off under reduced pressure, giving 12.2 g of a solid. A quantitative $^1$H-NMR spectrum gives the 4-hydroxybenzaldehyde content as 80% (80% of theoretical), the proportion of salicylaldehyde being less than 0.1%.

EXAMPLE 2

Preparation of 4-hydroxy-3-methylbenzaldehyde 10.8 g (100 mmol) of o-cresol are admixed in a 250 ml stainless-steel autoclave with 100 g (5 mol) of anhydrous hydrogen fluoride and 13.8 g (203 mmol) of boron trifluoride. Subsequently the reaction mixture is heated to 40° C. and carbon monoxide is passed in until the pressure has reached 100 bar. This pressure must be readjusted a number of times during the reaction time. After 14 hours the reaction solution is poured onto 1 kg of ice and is neutralized with concentrated KOH solution. Further workup as in Example 1 gave 13.5 g of an oil. The $^1$H-NMR spectrum and the gas chromatogram gave the purity of the 4-hydroxy-3-methylbenzaldehyde obtained as 95% (94% of theoretical).

EXAMPLE 3 (Comparative)

Preparation of 4-hydroxy-3-methylbenzaldehyde 10.8 g (100 mmol) of o-cresol are admixed in a 250 ml stainless-steel autoclave with 100 g (5 mol) of anhydrous hydrogen fluoride and 14 g (206 mmol) of boron trifluoride. Subsequently carbon monoxide is passed into the reaction mixture first at room temperature until the pressure has reached 100 bar. The mixture is then heated to 40° C. and stirred for 22 hours. The reaction solution is then poured onto 1 kg of ice and is neutralized with concentrated KOH solution. Further workup as in Example 1 gave 13.5 g of a product. The molar ratio of 4-hydroxy-3-methylbenzaldehyde to the isomeric 2-hydroxy-3-methylbenzaldehyde is 83:17 (82% and 17% respectively of theoretical).

EXAMPLE 4

Preparation of 4-hydroxy-3,5-dimethylbenzaldehyde 12.2 g (100 mmol) of 2,6-dimethylphenol are admixed in a 250 ml stainless-steel autoclave with 100 g (5 mol) of anhydrous hydrogen fluoride and 14.5 g (213 mmol) of boron trifluoride. Subsequently carbon monoxide is passed into the reaction mixture at 22° C. until the pressure has reached 110 bar. This pressure must be readjusted a number of times during the reaction time. After one hour the reaction solution is poured onto 1 kg of ice and is neutralized with concentrated KOH solution. Further workup as in Example 1 gave 14.8 g of a solid which the $^1$H-NMR spectrum shows to be 4-hydroxy-3,5-dimethylbenzaidehyde. The purity of this compound obtained was 98% (97% of theoretical).

If the 2,6-dimethylphenol is charged as a solution in methylene chloride, chloroform or carbon tetrachloride and the procedure is otherwise as described in this example, practically the same result is obtained.

EXAMPLE 5

Preparation of 2-hydroxy-4,5-dimethylbenzaldehyde 12.2 g (100 mmol) of 3,4-dimethylphenol are admixed in a 250 ml stainless-steel autoclave with 100 g (5 mol) of anhydrous hydrogen fluoride and 14.2 g (208 mmol) of boron trifluoride. Subsequently the reaction mixture is heated to 40° C. and carbon monoxide is passed in until the pressure has reached 110 bar. This pressure must be readjusted a number of times during the reaction time. After 22 hours the reaction solution is poured onto 1 kg of ice and is neutralized with concentrated KOH solution. Further workup as in Example 1 gave 14.8 g of 2-hydroxy-4,5-dimethylbenzaldehyde, the purity of which is determined by gas chromatography to be 98% (97% of theoretical). The formation of the isomers of the main component, 5,6-dimethyl-2-hydroxybenzaldehyde, is not observed here.

EXAMPLE 6 (Comparative Example)

Preparation of 2-hydroxy-4,5-dimethylbenzaldehyde 12.2 g (100 mmol) of 3,4-dimethylphenol are admixed in a 250 ml stainless-steel autoclave with 100 g (5 mol) of anhydrous hydrogen fluoride and 14 g (206 mmol) of boron trifluoride. Subsequently carbon monoxide is passed into the reaction mixture first at room temperature until the pressure has reached 100 bar. The mixture is then heated to 40° C. and stirred for 22 hours. The reaction solution is then poured onto 1 kg of ice and is neutralized with concentrated KOH solution. Further workup as in Example 1 gave 13.5 g of a solid, comprising 2-hydroxy-4,5-dimethylbenzaldehyde and 5,6-dimethyl-2-hydroxybenzaldehyde in a ratio of 95:5 (85% and 4.5% respectively of theoretical).

EXAMPLE 7

Preparation of 3-hydroxy-5,6,7,8-tetrahydro-2-naphthaldehyde 5 g (33.7 mmol) of 5,6,7,8-tetrahydro-2-naphthol are admixed in a 250 ml stainless-steel autoclave with 50 g (2.5 mol) of anhydrous hydrogen fluoride and 5 g (73 mmol) of boron trifluoride. Subsequently the reaction mixture is heated to 40° C. and carbon monoxide is passed in until the pressure has reached 150 bar. This pressure must be readjusted a number of times during the reaction time. After 18 hours the reaction solution is poured onto 1 kg of ice and is neutralized with concentrated KOH solution. Further workup as in Example 1 gave 5.7 g of a solid, the $^1$H-NMR spectrum of which is in agreement with that of 5,6,7,8-tetrahydro-2-naphthaldehyde as comparison material. The GC purity is 95% (91% of theoretical).

If the 5,6,7,8-tetrahydro-2-naphthol is charged as a solution in dichloromethane, hexane or heptane and the procedure is otherwise as described in this example, practically the same result is obtained.

EXAMPLE 8

Preparation of 4-hydroxy-3-ethylbenzaldehyde 12.2 g (100 mmol) of 2-ethylphenol are admixed in a 250 ml stainless-steel autoclave with 100 g (5 mol) of anhydrous hydrogen fluoride and 14.5 g (212 mmol) of boron trifluoride. Subsequently the reaction mixture is heated to 40° C. and carbon monoxide is passed in until the pressure has reached 50 bar. This pressure must be readjusted a number of times during the reaction time. After 1 hour the reaction solution is poured onto 1 kg of ice and is neutralized with concentrated KOH solution. Further workup as in Example 1 gave 10.6 g of a brown oil which is characterized as 4-hydroxy-3-ethylbenzaldehyde. The purity determined by gas chromatography is 95% (91% of theoretical).

What is claimed is:

1. A process for preparing hydroxybenzaldehydes of the general formula (1)

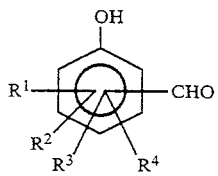
(1)

in which $R^1$, $R^2$, $R^3$ and $R^4$ are identical or different and are hydrogen, fluorine, chlorine or bromine atoms, also alkyl($C_1$–$C_6$) groups which may be substituted by fluorine atoms, alkoxy($C_1$–$C_4$) groups, unsubstituted or substituted aryl($C_6$–$C_6$) groups, which may be substituted at the aromatic nucleus by fluorine, chlorine or bromine atoms or by alkyl($C_1$–$C_4$) or alkoxy($C_1$–$C_4$) groups, also unsubstituted or substituted aryl($C_6$–$C_{14}$)-alkyl($C_1$–$C_6$) groups, which may be substituted at the aromatic nucleus by fluorine, chlorine or bromine atoms or by alkyl($C_1$–$C_4$) or alkoxy($C_1$–$C_4$) groups, also a cyclopentyl, cyclopentadienyl, cyclohexyl, cyclohexenyl or cyclohexadienyl group which may be substituted by alkyl($C_1$–$C_4$) groups, also the phenoxy group which may be substituted by fluorine, chlorine or bromine atoms or by alkyl($C_1$–$C_4$) or alkoxy($C_1$–$C_4$) groups, and where the substituents $R^1$, $R^2$, $R^3$ and $R^4$ may with the hydroxybenzene ring carbon atoms on which they are located form one or two saturated or unsaturated isocyclic or heterocyclic rings which may be substituted by alkyl($C_1$–$C_4$) groups, and in which the hydroxyl and aldehyde groups are in the ortho or para position with respect to one another, which comprises admixing 1 mol of a phenol of the general formula (2)

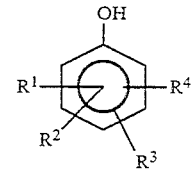
(2)

in which $R^1$, $R^2$, $R^3$ and $R^4$ have the meanings above, if desired in an organic solvent which is inert towards the reactants, in a pressure vessel with from about 5 to about 100 mol of hydrogen fluoride and from about $0.5+x$ to about $1.5+x$ mol of boron trifluoride, where $x$ is the number of oxygen atoms contained in the starting compound of the stated formula (2), setting the temperature of this mixture to from about $-10°$ to about $100°$ C. and subsequently passing carbon monoxide into this initially charged mixture until a pressure of from about 10 to about 150 bar is reached and allowing the mixture to react at the desired pressure reached.

2. The process as claimed in claim 1, wherein from about 20 to about 50 mol of hydrogen fluoride are used.

3. The process as claimed in claim 1, wherein the reaction is carried out with from about $0.9+x$ to about $1.2+x$, where x has the meaning given in claim 1, mol of boron trifluoride.

4. The process as claimed in claim wherein 1 mol of boron trifluoride is used.

5. The process as claimed in claim 1 wherein the reaction is carried out at temperatures of from about 0° to about 80° C.

6. The process as claimed in claim 1 wherein the reaction is carried out at a CO pressure of from about 20 to about 100 bar.

7. The process as claimed in claim 1, wherein the set CO pressure is readjusted if it falls during the reaction.

8. The process as claimed in claim 1 wherein the initial charge comprises the compound of the stated general formula (2) dissolved in an organic solvent which is inert towards the reactants.

9. The process as claimed in claim 1, wherein the initial charge comprises the compound of the stated general formula (2) dissolved in methylene chloride, chloroform, carbon tetrachloride, dichloroethane, hexane or heptane.

10. The process as claimed in claim 1 wherein the order of addition is hydrogen fluoride, compound of the formula (2), boron trifluoride.

11. The process as claimed in claim 1, wherein at least one of $R^1$, $R^2$, $R^3$ and $R^4$ is selected from unsubstituted or substituted phenyl or unsubstituted or substituted naphthyl or; unsubstituted or substituted phenylalkyl($C_1$–$C_6$) or unsubstituted or substituted naphthyl-alkyl($C_1$–$C_6$) groups.

12. The process as claimed in claim 1, wherein the reaction is carried out with pure anhydrous hydrogen fluoride in the absence of an inert solvent.

13. The process as claimed in claim 1, wherein the reaction is carried out in a reaction time from about 30 minutes to about 50 hours.

14. The process as claimed in claim 1, wherein the reaction is carried out in a reaction time from about 1 hour to about 24 hours.

15. The process as claimed in claim 1, wherein the compound of the general formula (2) is introduced first and the hydrogen fluoride is then added.

16. The process as claimed in claim 1, wherein 4-hydroxybenzaldehyde is produced.

17. The process as claimed in claim 1, wherein 4-hydroxy-3-methylbenzaldehyde, 4-hydroxy-3,5-diemthylbenzaldehyde,2-hydroxy-4,5-diemthylbenzaldehyde, 3-hydroxy-5,6,7, 8-tetrahydro-2-naphthaldehyde or 4-hydroxy-3-ethylbenzadehyde are produced.

* * * * *